United States Patent
Ganapathy et al.

(10) Patent No.: US 9,033,905 B2
(45) Date of Patent: May 19, 2015

(54) PNEUMATIC COMPRESSION GARMENT WITH NOISE ATTENUATING MEANS

(71) Applicant: Covidien LP, Mansfield, MA (US)

(72) Inventors: Premnarayan Ganapathy, Brookline, MA (US); Steven Nardi, Taunton, MA (US); Paul Becker, Taunton, MA (US)

(73) Assignee: Covidien LP, Mansfield, MA (US)

( * ) Notice: Subject to any disclaimer, the term of this patent is extended or adjusted under 35 U.S.C. 154(b) by 53 days.

(21) Appl. No.: 13/896,560

(22) Filed: May 17, 2013

(65) Prior Publication Data
US 2014/0142481 A1    May 22, 2014

Related U.S. Application Data

(62) Division of application No. 12/569,318, filed on Sep. 29, 2009, now Pat. No. 8,469,910.

(51) Int. Cl.
*A61H 9/00* (2006.01)
*A61B 17/132* (2006.01)
(Continued)

(52) U.S. Cl.
CPC .............. *A61H 9/0078* (2013.01); *A61H 9/005* (2013.01); *A61B 17/1325* (2013.01); *A61B 17/135* (2013.01); *A61F 5/0111* (2013.01); *A61F 5/012* (2013.01); *A61F 5/34* (2013.01);
(Continued)

(58) Field of Classification Search
CPC ....... A61H 9/00; A61H 9/005; A61H 9/0078; A61H 9/0092
USPC ............... 601/151, 148, 84, 88, 96, 105, 152, 601/149, 150, 9, 46; 602/13, 23; 128/847, 128/867, 868; 181/230
See application file for complete search history.

(56) References Cited

U.S. PATENT DOCUMENTS

| | | |
|---|---|---|
| 3,677,300 A | 7/1972 | King |
| 3,736,074 A | 5/1973 | Kilbane et al. |

(Continued)

FOREIGN PATENT DOCUMENTS

| | | |
|---|---|---|
| EP | 0 897 707 A2 | 2/1999 |
| GB | 2271060 A | 4/1994 |
| GB | 0217996.8 | 8/2002 |

OTHER PUBLICATIONS

Restriction Requirement dated Jun. 19, 2012 relating to U.S. Appl. No. 12/569,318, 6 pages.

(Continued)

*Primary Examiner* — Justine Yu
*Assistant Examiner* — Colin W Stuart
(74) *Attorney, Agent, or Firm* — John Paul Mello, Esq.

(57) ABSTRACT

A pneumatic compression garment includes a flexible member for placement on a limb of a human body. A bladder in the flexible member defines an inflatable chamber. The bladder has an opening through which the inflatable chamber is inflated. A port mounted on the bladder has an air inlet adapted for communication with a source of pressurized air and an air outlet in communication with the inflatable chamber via the opening in the bladder. Pressurized air is delivered from into the inflatable chamber for inflating the inflatable chamber and thereby applying a compression force to the limb when the flexible member is in place on the limb. An air diverter affixed to an inside surface of a first sheet of the bladder and configured to divert air entering the inflatable chamber from directly impinging against an inside surface of a second sheet of the bladder.

11 Claims, 10 Drawing Sheets

(51) Int. Cl.
*A61B 17/135* (2006.01)
*A61F 5/01* (2006.01)
*A61F 5/34* (2006.01)

(52) U.S. Cl.
CPC ....... *A61H 9/0092* (2013.01); *A61H 2201/165* (2013.01); *A61H 2205/12* (2013.01); *A61H 9/00* (2013.01)

(56) References Cited

U.S. PATENT DOCUMENTS

| | | | |
|---|---|---|---|
| 3,855,910 A | 12/1974 | Brinton et al. | |
| 3,944,084 A | 3/1976 | Reeves | |
| 3,946,735 A | 3/1976 | DeWall | |
| 4,135,500 A | 1/1979 | Gorran | |
| 4,264,282 A | 4/1981 | Crago | |
| 4,399,739 A | 8/1983 | Dean | |
| 4,418,443 A | 12/1983 | Fischer | |
| 4,435,877 A | 3/1984 | Berfield | |
| 4,450,933 A | 5/1984 | Fukuoka et al. | |
| 4,534,343 A | 8/1985 | Nowacki et al. | |
| 4,606,328 A | 8/1986 | Thoman | |
| 4,729,722 A | 3/1988 | Toth | |
| 4,872,448 A | 10/1989 | Johnson, Jr. | |
| 4,888,003 A | 12/1989 | Johnson et al. | |
| 4,911,697 A | 3/1990 | Kerwin | |
| 4,921,477 A | 5/1990 | Davis | |
| 4,991,617 A | 2/1991 | Butler | |
| 5,047,072 A | 9/1991 | Wertz et al. | |
| 5,118,262 A | 6/1992 | Kuo | |
| 5,147,243 A | 9/1992 | Inglis et al. | |
| 5,174,127 A | 12/1992 | Harper et al. | |
| 5,214,253 A | 5/1993 | Houston, Jr. | |
| 5,260,524 A | 11/1993 | Schroeder et al. | |
| 5,285,791 A | 2/1994 | Smith | |
| 5,353,525 A | 10/1994 | Grim | |
| 5,354,260 A | 10/1994 | Cook | |
| 5,449,379 A | 9/1995 | Hadtke | |
| 5,599,333 A | 2/1997 | Atkinson | |
| 5,628,306 A | 5/1997 | Kee | |
| 5,804,777 A | 9/1998 | Kim et al. | |
| 5,840,400 A * | 11/1998 | Landi et al. | 428/116 |
| 5,858,062 A | 1/1999 | McCulloh et al. | |
| 5,961,309 A | 10/1999 | Harpole et al. | |
| 5,996,731 A | 12/1999 | Czabala et al. | |
| 6,089,346 A | 7/2000 | Tredinnick et al. | |
| 6,126,393 A | 10/2000 | Arnold | |
| 6,231,009 B1 | 5/2001 | Kong | |
| 6,280,153 B1 | 8/2001 | Iversen et al. | |
| 6,340,069 B1 | 1/2002 | Wang | |
| 6,382,931 B1 | 5/2002 | Czabala et al. | |
| 6,447,491 B1 | 9/2002 | Lord | |
| 6,558,137 B2 | 5/2003 | Tomell et al. | |
| 6,579,075 B2 | 6/2003 | Lee et al. | |
| 6,623,239 B2 | 9/2003 | Sahay et al. | |
| 6,663,596 B2 | 12/2003 | Griego et al. | |
| 6,682,317 B2 | 1/2004 | Chen | |
| 6,702,880 B2 | 3/2004 | Roberts et al. | |
| 6,740,066 B2 | 5/2004 | Wolff et al. | |
| 6,743,250 B2 | 6/2004 | Renfro | |
| 6,840,746 B2 | 1/2005 | Marshall et al. | |
| 6,866,700 B2 | 3/2005 | Amann | |
| 6,935,460 B2 | 8/2005 | McCombs et al. | |
| 6,966,198 B2 | 11/2005 | Piccirilli et al. | |
| 7,070,567 B2 | 7/2006 | Mizukoshi et al. | |
| 7,141,101 B2 | 11/2006 | Amann | |
| 7,153,107 B1 | 12/2006 | Maddox, Jr. | |
| 7,431,571 B2 | 10/2008 | Kim et al. | |
| 7,452,340 B2 | 11/2008 | Cook et al. | |
| 7,931,606 B2 | 4/2011 | Meyer | |
| 7,967,766 B2 | 6/2011 | Ravikumar | |
| 8,328,741 B2 | 12/2012 | Ganapathy | |
| 2002/0085931 A1 | 7/2002 | Lee et al. | |
| 2004/0126247 A1 | 7/2004 | Broser et al. | |
| 2004/0261621 A1 | 12/2004 | Lindsay | |
| 2005/0067218 A1 | 3/2005 | Bristow et al. | |
| 2006/0111655 A1 | 5/2006 | Cook et al. | |
| 2006/0251527 A1 | 11/2006 | Wester | |
| 2007/0019047 A1 | 1/2007 | Kleinert et al. | |
| 2007/0135743 A1 | 6/2007 | Meyer | |
| 2007/0276313 A1 | 11/2007 | Moorehead et al. | |
| 2007/0290012 A1 | 12/2007 | Jackman | |
| 2008/0030747 A1 | 2/2008 | Shingai | |
| 2008/0082059 A1 | 4/2008 | Fink et al. | |
| 2008/0087169 A1 | 4/2008 | Clark | |
| 2008/0103422 A1 | 5/2008 | Perry et al. | |
| 2008/0200872 A1 | 8/2008 | Isham | |
| 2009/0062703 A1 | 3/2009 | Meyer et al. | |
| 2011/0077564 A1 | 3/2011 | Ganapathy et al. | |
| 2011/0077565 A1 | 3/2011 | Hanlon et al. | |

OTHER PUBLICATIONS

Response to Restriction Requirement dated Jul. 16, 2012 relating to U.S. Appl. No. 12/569,318, 1 page.
Non-Final Office Action dated Aug. 15, 2012 relating to U.S. Appl. No. 12/569,318, 27 pages.
Amendment A dated Nov. 5, 2012 relating to U.S. Appl. No. 12/569,318, 12 pages.
Final Office Action dated Nov. 28, 2012 relating to U.S. Appl. No. 12/569,318, 11 pages.
Response to Final Office Action dated Jan. 18, 2013 relating to U.S. Appl. No. 12/569,318, 13 pages.

* cited by examiner

PNEUMATIC COMPRESSION GARMENT WITH NOISE ATTENUATING MEANS

CROSS-REFERENCE TO RELATED APPLICATION

This application is a divisional of U.S. Ser. No. 12/569,318, filed Sep. 29, 2009, the entirety of which is incorporated herein by reference.

FIELD OF THE INVENTION

The present disclosure generally relates to a compression garment configured for applying compressive forces to a portion of a wearer's body. In particular, the present disclosure relates to a means for attenuating the noise generated from air flow into an inflatable chamber of the compression garment.

BACKGROUND OF THE INVENTION

Compression garments for applying compressive forces to a selected area of a wearer's body are generally employed to improve blood flow in the selected area. Compression garments in which intermittent pulses of compressed air are delivered to at least one inflatable chamber in a cuff or sleeve of the garment are particularly useful. This cyclic application of pressure provides a non-invasive method of prophylaxis to reduce the incidence of deep vein thrombosis (DVT) and improve blood flow.

In general, a compression garment of the type described above includes a flexible member having an inflatable bladder disposed therein. The compression garment is placed around the patient's foot or other selected limb, and a pressurized fluid or air is delivered into the inflatable bladder to create pressure at the part or parts of the body in contact with the bladder. The high velocity or flow rate of the pressurized fluid/air entering the bladder produces noise that can be unpleasant to the wearer of the compression device.

SUMMARY OF THE INVENTION

One aspect of the present invention is directed to a pneumatic compression garment comprising a flexible member for placement on a limb of a human body and a bladder in the flexible member. The bladder defines an inflatable chamber and has an opening through which the inflatable chamber is inflated. A port is mounted on the bladder. The port has an air inlet adapted for communication with a source of pressurized air and an air outlet in communication with the inflatable chamber via the opening in the bladder for delivery of air from the source of pressurized air into the inflatable chamber for inflating the inflatable chamber and thereby applying a compression force to the limb when the flexible member is in place on the limb. The compression garment further comprises noise attenuating means associated with the bladder opening for reducing noise from air flow through the opening into the inflatable chamber.

In another aspect of the invention, a pneumatic compression garment comprises a flexible member for placement on a limb of a human body and a bladder in the flexible member. The bladder defines an inflatable chamber and has an opening through which the inflatable chamber is inflated. A port mounted on the bladder has an air inlet adapted for communication with a source of pressurized air and an air outlet in communication with the inflatable chamber via the opening in the bladder. Pressurized air is delivered into the inflatable chamber for inflating the inflatable chamber and thereby applying a compression force to the limb when the flexible member is in place on the limb. The compression garment further comprises at least one flexible, resilient flap in registration with at least a portion of the air outlet of the port. The flap deflects when air is delivered into the inflatable chamber through the opening in the inflatable bladder.

In yet another aspect of the invention, a pneumatic compression garment comprises a flexible member for placement on a limb of a human body and a bladder in the flexible member. The bladder comprises first and second opposing sheets of flexible, air-impermeable material and defines an inflatable chamber. The bladder has an opening through which the inflatable chamber is inflated. A port is affixed to an outside surface of the first bladder sheet. The port has an air inlet adapted for communication with a source of pressurized air and an air outlet in communication with the inflatable chamber via the opening in the bladder. Pressurized air is delivered from the source of pressurized air into the inflatable chamber for inflating the inflatable chamber and thereby applying a compression force to the limb when the flexible member is in place on the limb. An air diverter formed of air-impermeable material is affixed to an inside surface of the first bladder sheet. The air diverter has an edge overlying at least a portion of the opening in the bladder and is configured to divert air entering the inflatable chamber from directly impinging against an inside surface of the second bladder sheet.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
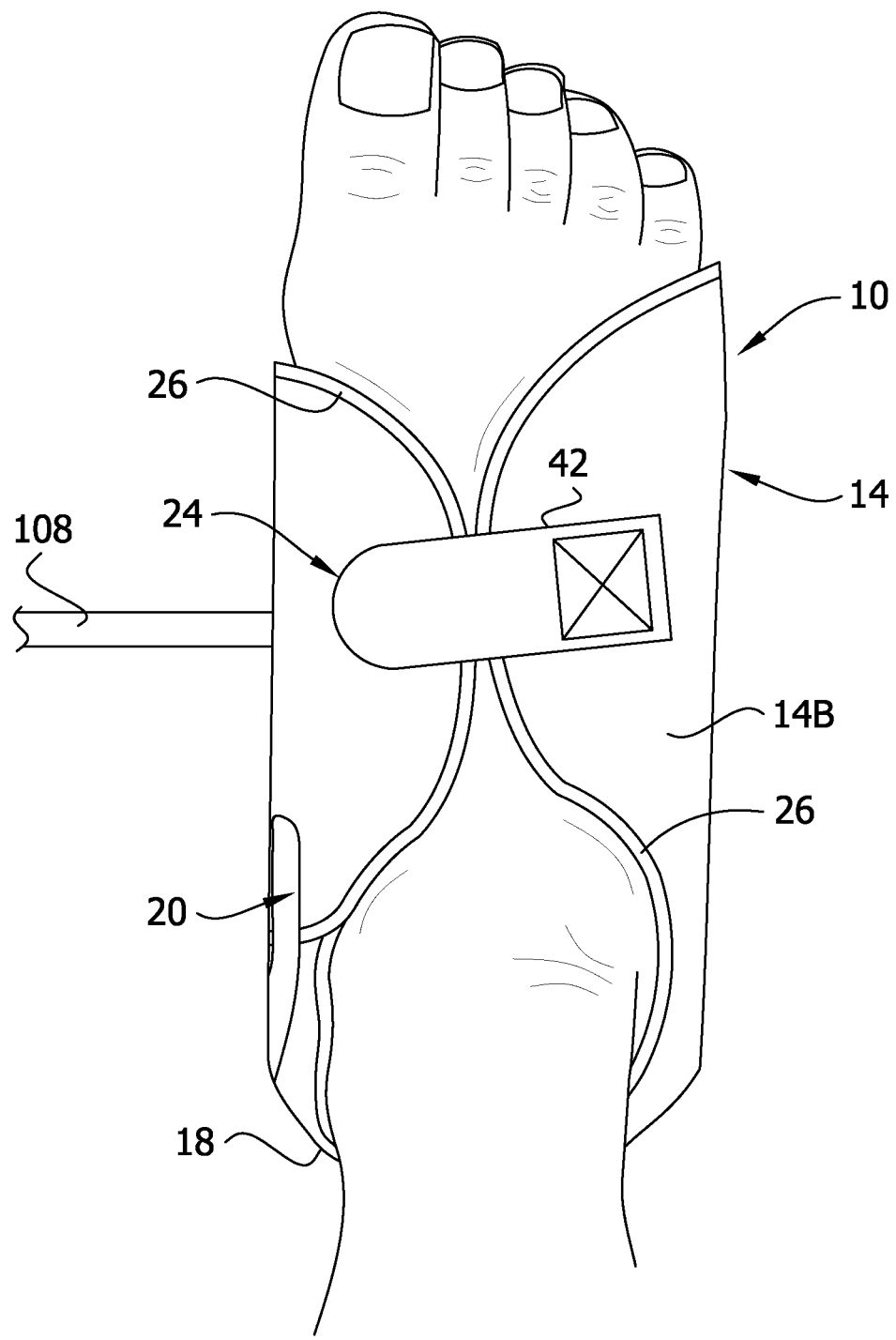
FIG. 1 is a top view of a compression garment as applied to a foot of a patient.
Figure 2:
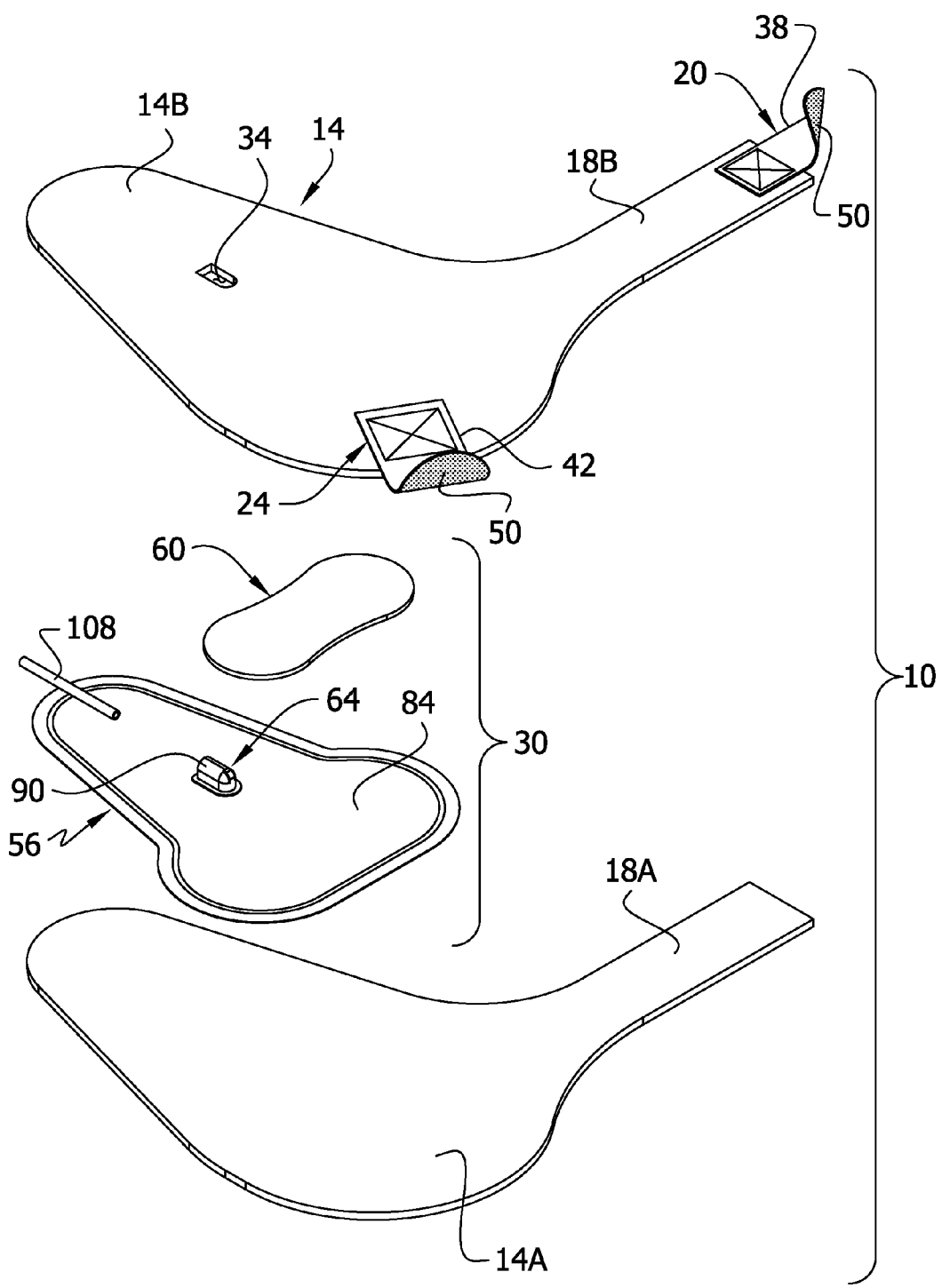
FIG. 2 is an exploded perspective of the compression garment of FIG. 1.
Figure 3:
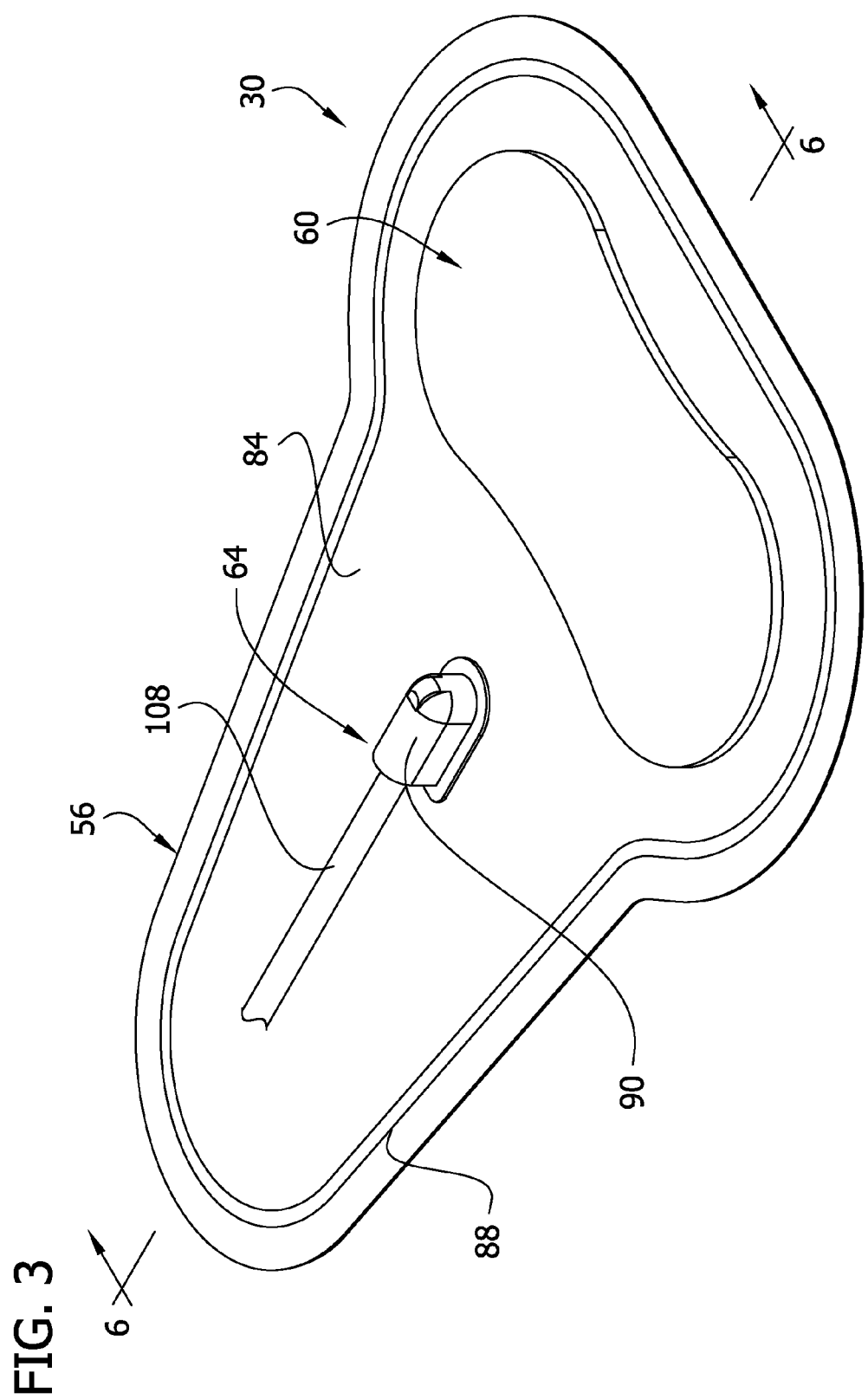
FIG. 3 is a bottom perspective of a first embodiment of a bladder assembly of the compression garment.

With reference to FIGS. 1 and 2, a first embodiment of a compression garment in accordance with the present disclosure is illustrated as a foot cuff and is designated generally as 10. The foot cuff 10 is adapted for use in a compression therapy system for applying compressive pressure to a foot of a wearer, as is generally known in the art and will not be described herein.

In general, the foot cuff 10 comprises a flexible member 14 configured to conform to the foot. The member 14 includes an ankle strap 18 and is secured in a self-retaining configuration on the foot by two releasable fasteners 20, 24, which are described in more detail below. It is understood that the foot cuff 10 may have other configurations within the scope of the present invention. It is also understood that compression garments other than foot cuffs are within the scope of the present invention, including but not limited to leg compression sleeves, arm compression sleeves, and similar devices. Moreover, although the present invention has particular application to garments that are cyclically inflated and deflated, it could be used in garments having different uses, such as for treating edema, wound healing, etc.

The flexible member 14 comprises an inner (contact) layer 14A and an outer layer 14B secured to one another along a line 26 generally adjacent corresponding perimeters of the layers to define an interior space for receiving and substantially enclosing a bladder assembly, generally designated 30. The inner and outer layers 14A, 14B may be fixedly secured to one another, such as by heat welding, adhesives, sewing, or other suitable ways. Alternatively, the layers 14A and 14B may be releasably secured to one another. In use, the inner layer 14A is adjacent to the wearer's foot and the outer layer 14B is located farthest from the foot. As used herein, the terms "inner" and "outer" indicate relative positions of respective components and surfaces with respect to the skin of the wearer's body part when the compression garment is secured to the body part, and as such, an "inner" component or surface is more adjacent to the skin of the body part than an "outer" component or surface.

The inner layer 14A and the outer layer 14B of the flexible member 14 include ankle strap portions 18A and 18B respectively. The ankle strap portions 18A, 18B have a longitudinally projecting configuration for wrapping about a portion of the foot adjacent to the ankle. The ankle strap portions 18A, 18B can be sewn, RF welded, or sonic welded to respective inner and outer layers 14A, 14B. However, in the illustrated embodiment, the ankle strap portions 18A, 18B are formed as one piece with the inner layer 14A and the outer layer 14B, respectively.

The inner layer 14A of the flexible member 14 is adapted for contacting the foot. In one embodiment, this layer 14A is fabricated from a chemically treated material, with wicking ability, for wicking moisture away from the skin. Furthermore, the inner layer 14A can be faced with a soft material toward the treatment surface of the wearer. For example, the soft material can be a thin layer of open celled porous foam, napped cloth, or a layer of vapor permeable cloth. It is understood that flexible members 14 not including an inner layer 14A or an outer layer 14B are within the scope of the present invention. Structure used to secure a bladder on a limb and maintain a position of the bladder can be a "flexible member."

Again referring to FIGS. 1 and 2, the outer layer 14B of the flexible member 14 includes an opening 34 for allowing passage of pressurized air to the bladder assembly 30. The outer layer 14B is configured for providing an attachment surface for a hook and loop feature of the foot cuff 10, as will be described in more detail below. Moreover, the outer layer 14B comprises a soft material for cushioning the top portion of the foot and may be fabricated from similar materials as the inner layer 14A and in similar dimensions therewith for corresponding geometry. Alternatively, the outer layer 14B may be fabricated from a laminated material, such as, for example, sontara fabric, open cell urethane foam, or loop fabric.

The releasable fasteners 20, 24 are positioned on and attached to the outer layer 14B of the foot cuff for securing the foot cuff 10 around the foot. The first fastener 20 comprises a tab 38 attached to the ankle strap portion 18B of the outer layer 14B of the foot cuff 10, and the second fastener 24 comprises a tab 42 attached to a surface of the outer layer 14B. Both straps 38, 42 have hook elements 50. In use, when the ankle strap 18 is wrapped about the back of the foot, the hook elements 50 on the straps engage loop elements (not shown) on the outer layer 14B of the foot cuff 10 to secure the cuff on the foot, as will be understood by those skilled in the field familiar with foot cuffs. The releasable fasteners 20, 24 may have portions (not shown) without fastening material thereon to provide convenient gripping locations on the hook fasteners so that the practitioner can readily separate the hooks 50 from the outer layer 14B. Other fastening structure may be used without departing from the scope of the present invention.

Referring to FIGS. 2-6, the bladder assembly 30 is enveloped and enclosed by the flexible member 14. The assembly 30 comprises an inflatable bladder 56, a substantially rigid sole 60, and a port 64 having an air inlet 68 and air outlet 72. The bladder 56 defines an inflatable chamber 76 and has an opening 78 through which the inflatable chamber is inflated. The port 64 is mounted on the bladder 56 and is adapted for communication with a source of pressurized air (not shown). The air outlet 72 of the port 64 is in fluid communication with the inflatable chamber 76 via the opening 78 in the bladder 56 for delivery of air from the source of pressurized air into the inflatable chamber. Inflation of the inflatable chamber 76 applies a compression force to a foot of a wearer.

Figure 4:
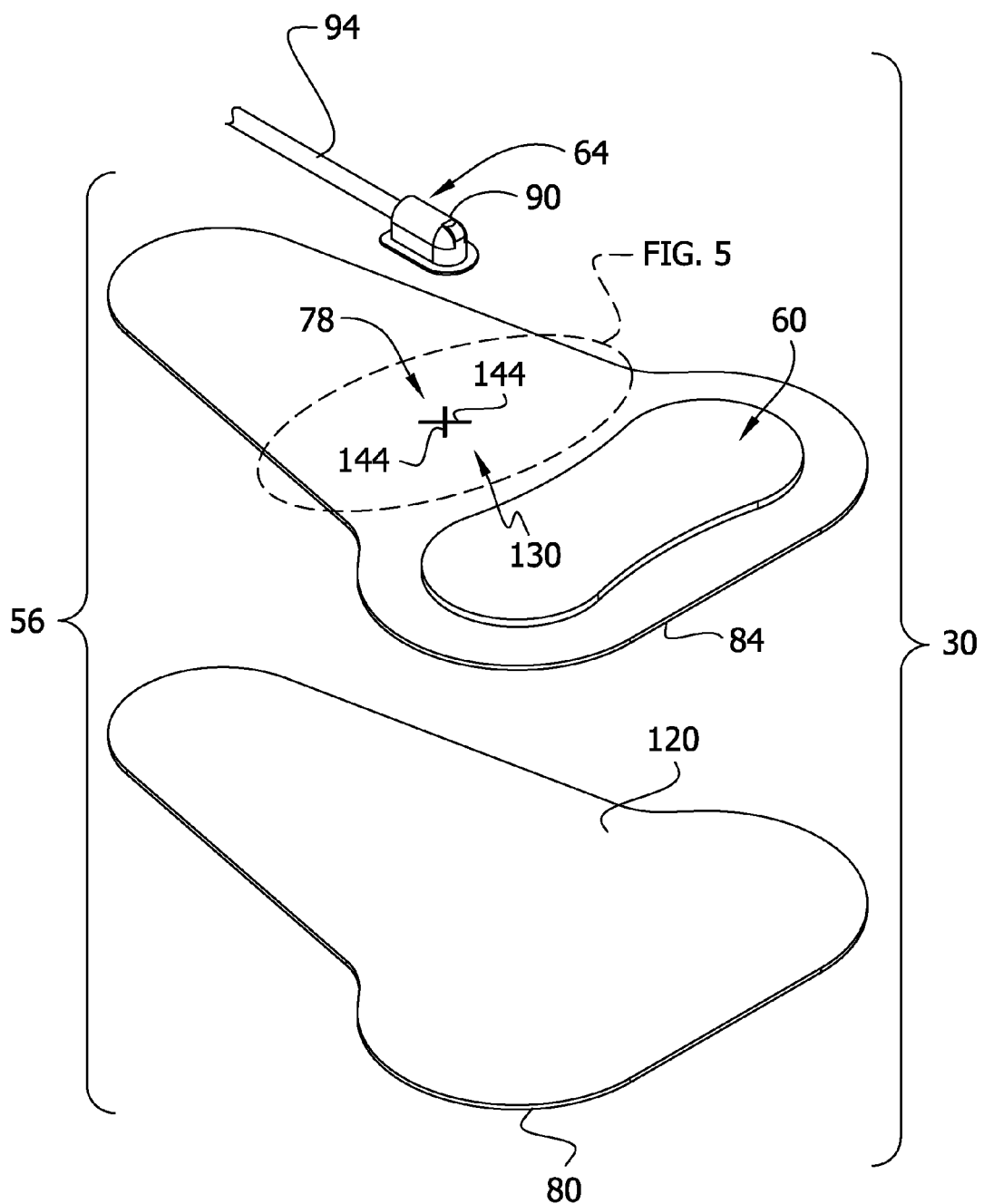
FIG. 4 is an exploded perspective of components of the bladder assembly of FIG. 3.
Figure 5:
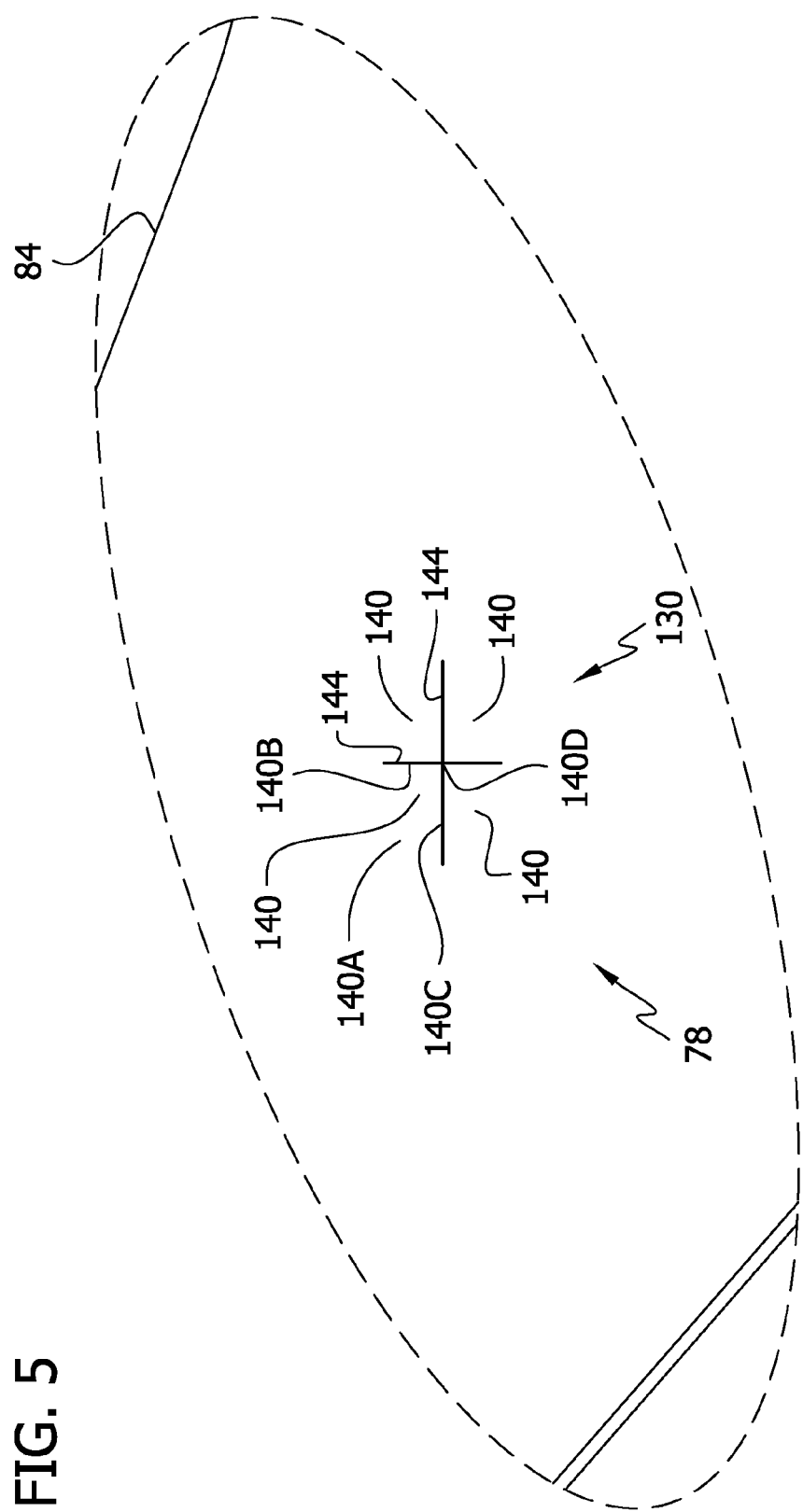
FIG. 5 is a plan view of an outer bladder sheet of the bladder assembly of FIG. 4.

Still referring to FIGS. 2-6, the bladder 56 includes inner and outer opposing sheets 80, 84 of flexible air-impermeable material (e.g., PVC) joined together in a suitable manner along a line 88 adjacent to their peripheries to define the inflatable chamber 76 (FIG. 5). As best illustrated in FIG. 2, the bladder 56 is positioned on the flexible member 14 such that the inflatable chamber 76 underlies the sole of the foot when the foot cuff is placed on the foot. The inflatable chamber 76 is adapted for receiving and retaining pressurized air for exerting compressive pressure on the foot during successive pressure application cycles, as will be understood by those skilled in this field. The opposing sheets 80, 84 of the bladder 56 are joined to one another in a suitable manner, such as by RF welding. Other ways of joining the sheets 80, 84 include sewing, adhesive, heat sealing, etc. It is understood that the bladder 56 can have other configurations within the scope of this invention. For example, the bladder may be formed from one or more sheets and/or may include more than one inflatable chamber.

The sole 60 of the bladder assembly 30 is a substantially rigid member positioned between the outer sheet 84 of the bladder 56 and the outer sheet 14B of the flexible member 14, and it extends generally lengthwise of the bottom of the foot when the foot cuff 10 is worn. The sole 60 provides a substantially rigid foundation against which the bladder 56 reacts during expansion. As a result, the expansion of the bladder 56 is directed toward the inner layer 14A of the flexible member 14 and the user's foot. The sole 60 is secured by suitable structure to maintain it in proper position relative to the bladder 56. It will be understood that the sole 60 may be omitted without departing from the scope of the present invention.

In the illustrated embodiment, the port 64 comprises an elbow member 90. The elbow member 90 is of suitable material (e.g., plastic) and has passage 100 extending through it to permit flow of air from one end of the member 102, constituting its inlet end, to an opposite end 106 of the member, constituting its outlet end. A tube 108 is attached to the inlet 68 at the inlet end 102 of the elbow member 90 for connection to the source of pressurized air (e.g., an air compressor) for delivery of pressurized air to the elbow member. The outlet end 106 of the elbow member 90 is attached to the outer sheet 84 of the bladder 56, and is aligned with the opening 78 in the outer bladder sheet 84 for delivery of air into the inflatable chamber 76 of the bladder. The opening 78 is described in further detail below. The tube 108 is attached and sealed to the elbow member 90 by suitable means, such as heat sealing, RF welding, or adhesive, for example. The elbow member 90 is attached and sealed to the bladder 56 by similar means, e.g., heat sealing, RF welding, solvent bond or adhesive. Other port configurations are within the scope of the present invention.

Figure 6:
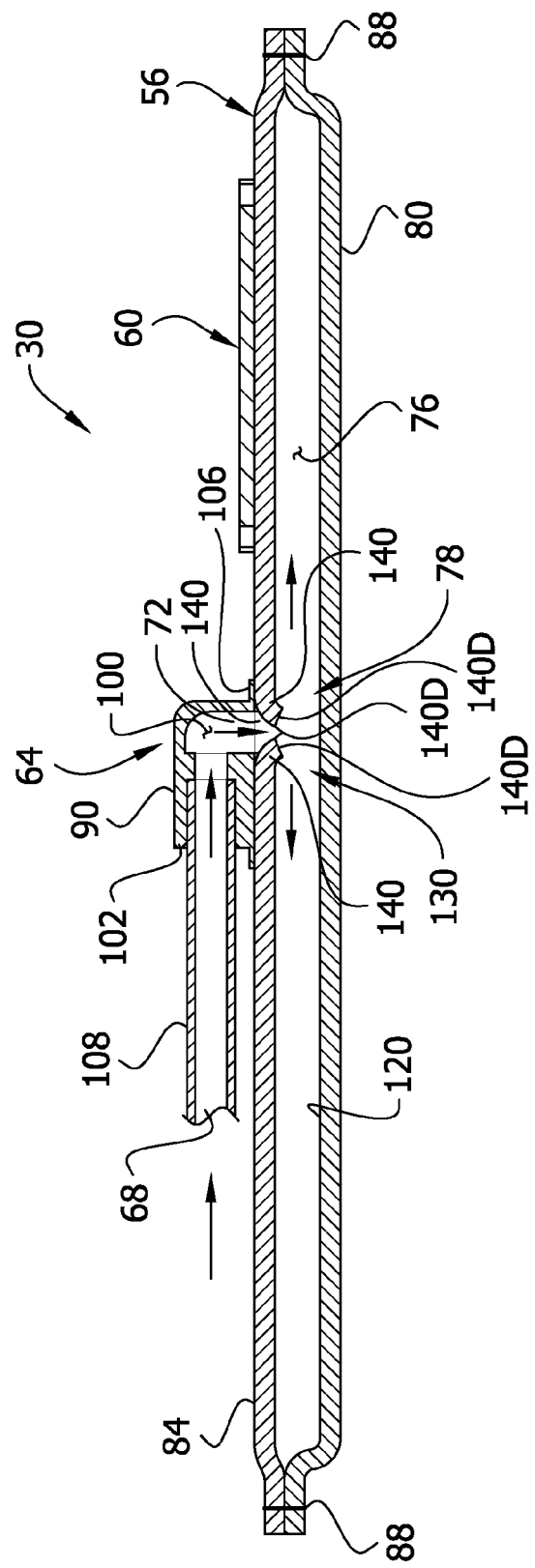
FIG. 6 is a section of the bladder assembly taken in the plane including line 5-5 in FIG. 3 and illustrating air flow into the bladder assembly.

As can be seen in FIGS. 4 and 6, the bladder 56 has an internal air impingement surface 120 inside the inflatable chamber 76 opposing the air outlet 72 of the port 64. In particular, the air impingement surface 120 is the surface of the inner bladder sheet 80 facing the inflatable chamber 76. During inflation of the inflatable chamber 76, noise is generated as pressurized air delivered through the bladder opening 78 impinges upon the impingement surface 120.

Noise attenuating means 130 associated with the bladder opening 78 is provided for reducing noise from air flow into the inflatable chamber 76 and impinging against the impingement surface 120. In the embodiment shown in FIGS. 1-6, the noise attenuating means 130 comprises four flaps 140. In the illustrated embodiment, the flaps 140 are formed as one piece with the outer bladder sheet 84. The bladder opening 78 comprises two linear slits 144 that form an X-shape. Thus, as shown in FIG. 5, each flap 140 is generally triangular, having a base 140A formed as one piece with the outer bladder sheet 84 and two free edges 140B, 140C forming a point 140D. The flaps 140 are flexible and air-impermeable.

The flaps 140 are positioned relative to the bladder opening 78 so that the flaps deflect when air is delivered into the inflatable chamber 76 through the bladder opening. The flaps 140 overlie at least a portion of the air outlet 72 of the port 64, and in the illustrated embodiment, the flaps overlie substantially all of the air outlet of the port. As shown in FIGS. 4 and 5, the flaps 140 have a relaxed position in which the flaps are substantially parallel with the opening 78 in the bladder 56. In this position, the free edges 140B, 140C of respective flaps 140 contact each other and the points 140D of the flaps contact each other. As shown in FIG. 6, the flaps 140 are in registration with the port outlet 72 so that as air is delivered into the inflatable chamber 76 through the bladder opening 78, the air moves the flaps 140 to a deflected position in which the flaps are not parallel to the bladder opening. The flaps 140 diffuse or dissipate energy of the compressed air as it enters the inflatable chamber 76, thus reducing noise generated during inflation of the inflatable chamber. The noise generation is reduced at least in part because the air entering the inflatable chamber 76 impinges upon the impingement surface 120 with less force. The flaps 140 are preferably resilient so they move back to or near their relaxed position (FIGS. 4 and 5) when air is not flowing into or out of the inflatable chamber 76. The flaps 140 allow air from within the inflatable chamber 76 to pass through the bladder opening 78 (e.g., deflect in an opposite direction than shown in FIG. 6) to deflate the inflatable chamber. Optionally, a hole (e.g., a circular hole having a diameter of approximately ⅛ in. (0.32 cm)) (not shown) may be formed at the intersection of the two slits 144 so that the points 140D of the flaps 140 are truncated. Such a configuration allows air to move past the flaps 140 move easily and ensures the flaps do not act as a check valve that obstructs deflation of the bladder 56.

Figure 7:
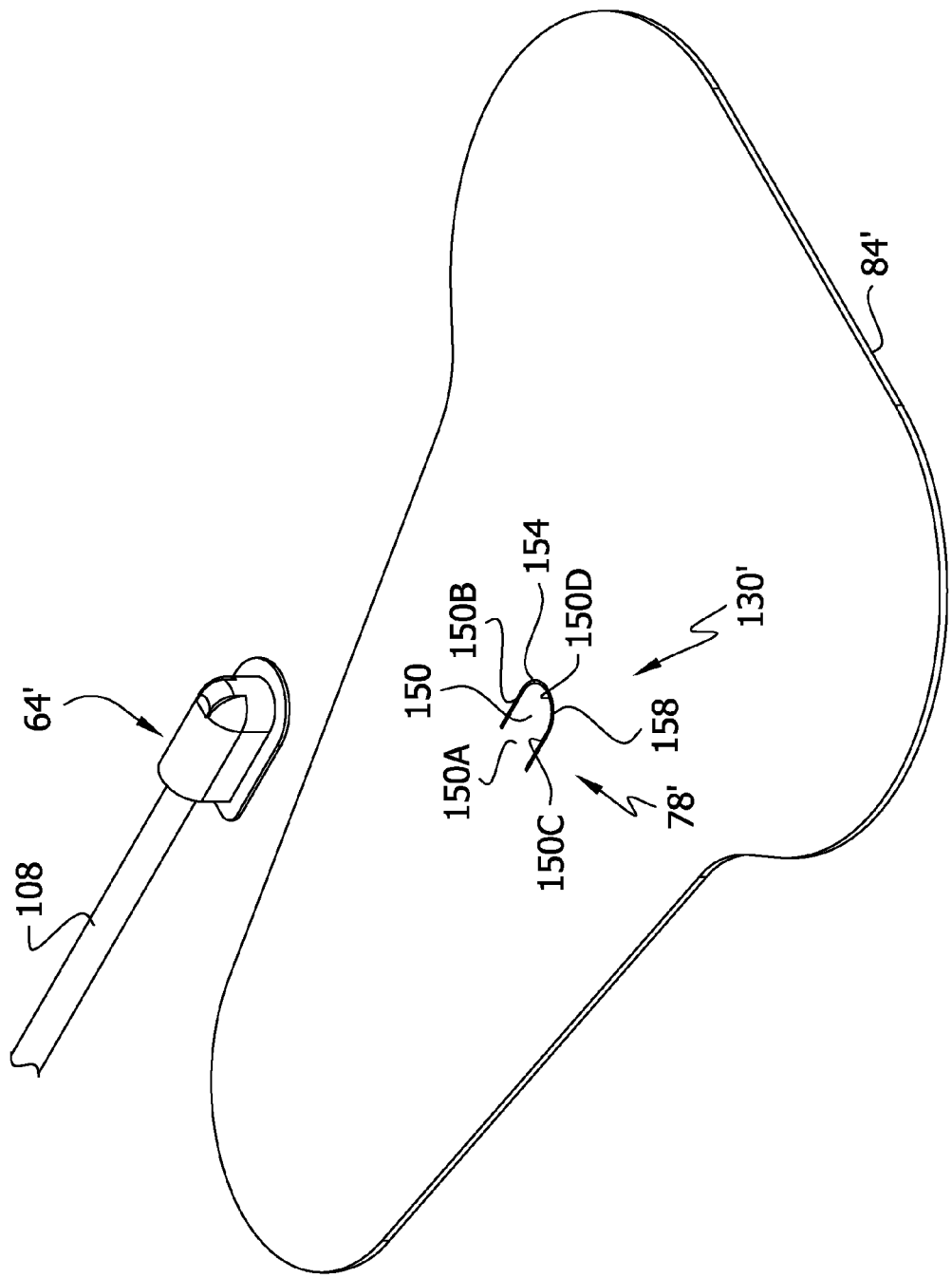
FIG. 7 is an exploded perspective of an outer bladder sheet, port and tube of the compression garment.
Figure 8:
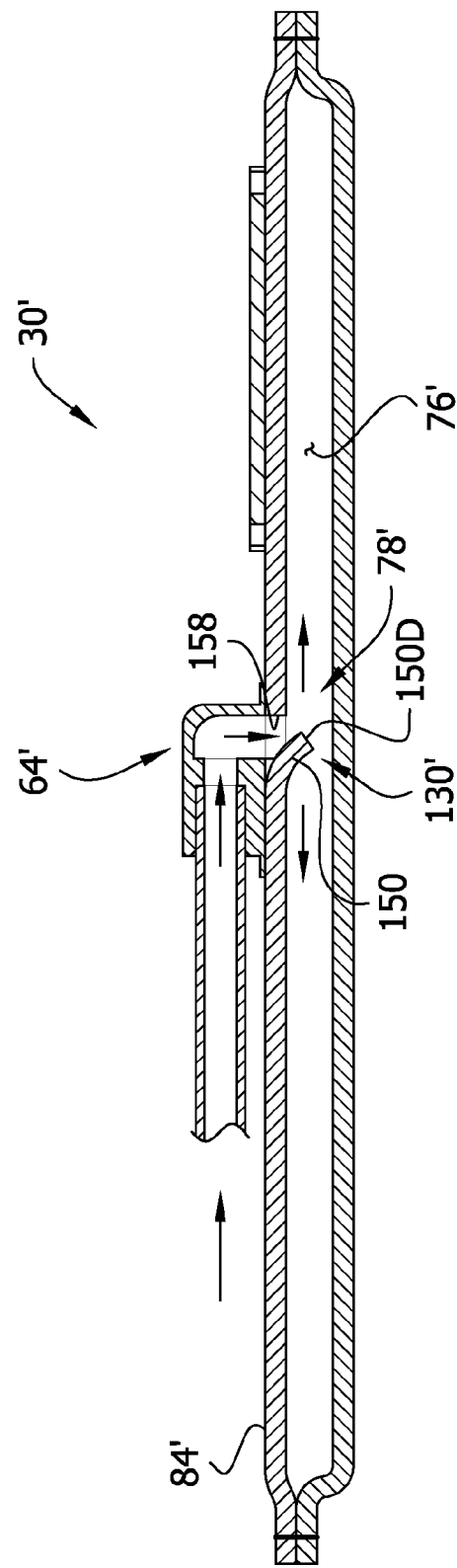
FIG. 8 is a section of the bladder assembly of FIG. 7 similar to FIG. 3.

FIGS. 7 and 8 illustrate a second embodiment of a bladder assembly 30' of the present invention. The bladder assembly 30' is substantially similar to the bladder assembly 30 described above, and corresponding parts are generally indicated by the same reference numbers, plus a prime designator ('). In this embodiment, the noise attenuating means 130' comprises a single flap 150. The bladder opening 78' comprises a U-shaped slit 154. Thus, the flap 150 has a base 150A formed as one piece with the outer bladder sheet 84' and free edges comprising linear side edges 150B, 150C and a curved distal edge 150D. As with the flaps 140 described above, the flap 150 has a relaxed position (FIG. 7) and a deflected position (FIG. 8). In the relaxed position, the flap 150 contacts an opposite edge 158 of the bladder opening 78'. The flap 150 diffuses or dissipates energy of the compressed air as it enters the inflatable chamber 76' from the port 64', thus reducing the noise generated during inflation of the inflatable chamber. Optionally, the distal edge 150D of the flap 150 may be truncated to provide an opening (not shown) between the flap and the opposite edge 158 of the bladder opening 78' to allow air to flow more easily past the flap and ensure the flap does not act as a check valve that obstructs deflation of the bladder 56.

Flaps having other configurations are within the scope of the present invention. For example, when the flaps 140 are in the relaxed position (FIG. 4), the free edges 140B, 140C need not touch each other. In addition, when the flap 150 is in the relaxed position (FIG. 6), free edges 150B-450D need not contact an opposing edge 158 of the bladder opening 78'. In other words, the bladder opening may comprise a gap between flaps and/or an opposing edge of the bladder opening. For example, the slits 144, 154 comprising the bladder opening 76, 76' may be wider than illustrated. In addition, a multitude of other slit configurations may be used to define other shapes, sizes and/or numbers of flaps. Linear segments and/or curved segments may be used to form any shape of slit. For example and not by limitation, other slit configurations may comprise the shape of an E, H, K, M, N, T, W, Y, Z or asterisk. Moreover, the flaps need not be formed as one piece with the bladder. The flaps may be formed separately from the bladder and suitably secured in position relative to the port outlet, such as in the following embodiment.

Figure 9:
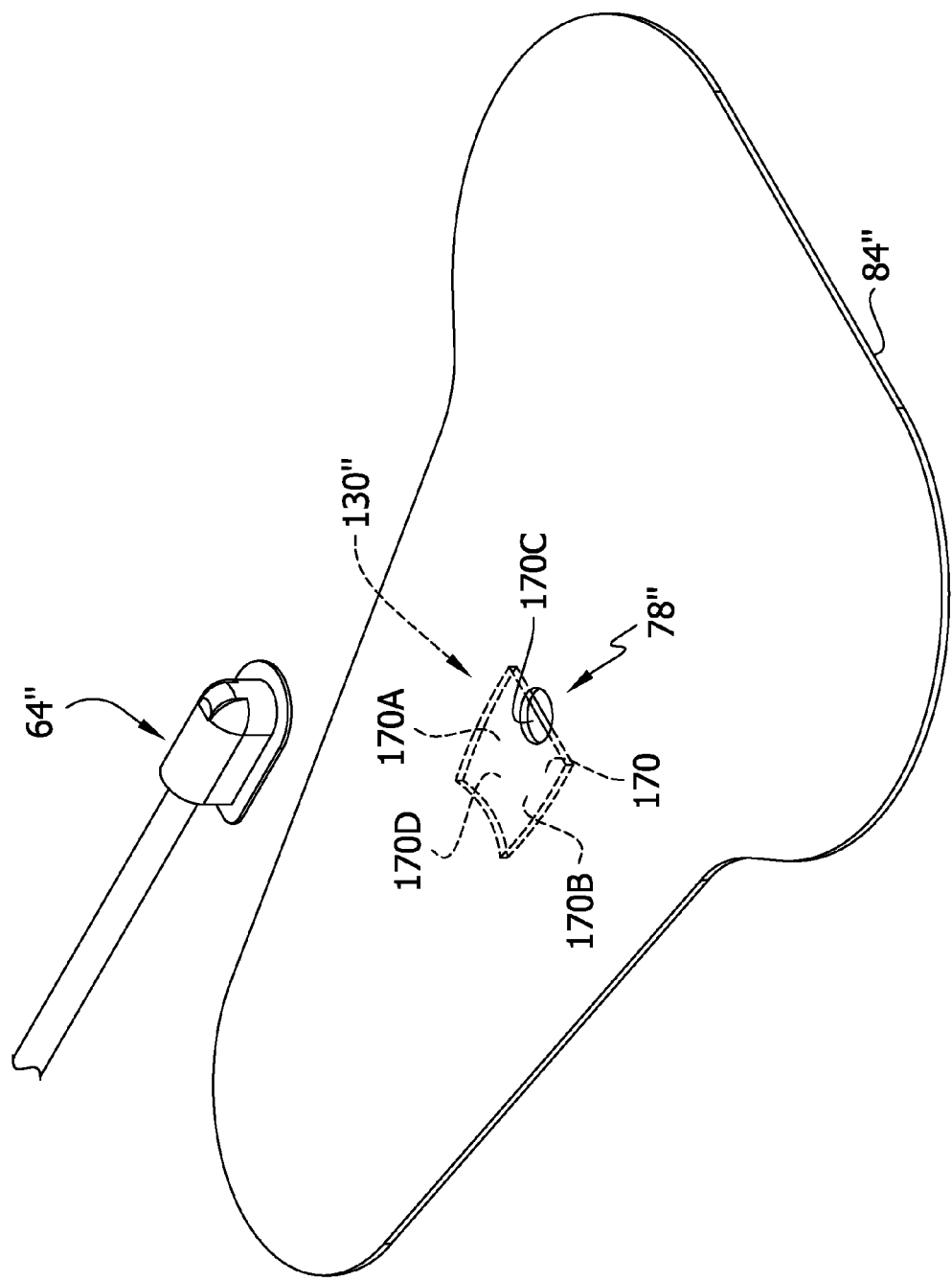
FIG. 9 is an exploded perspective of an outer bladder sheet, port and tube of the compression garment.
Figure 10:
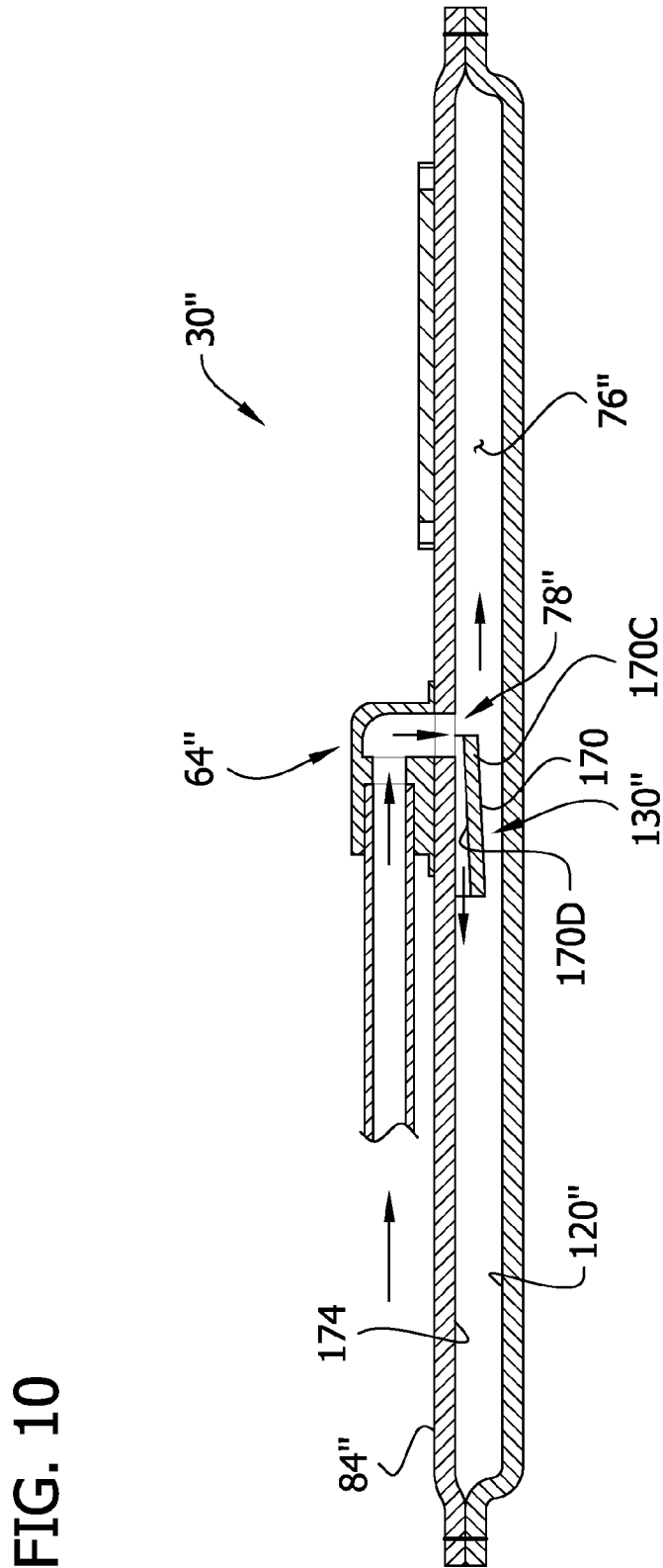
FIG. 10 is a section of the bladder assembly of FIG. 9 similar to FIG. 3.

FIGS. 9 and 10 illustrate a third embodiment of a bladder assembly 30" of the present invention. The bladder assembly 30" is similar to the bladder assembly 30 described above, and corresponding parts are generally indicated by the same reference numbers, plus a double prime designator ("). In this embodiment, the noise attenuating means 130" comprises an air diverter 170 positioned within the inflatable chamber 76". More specifically, the air diverter 170 is affixed to an inside surface 174 of the outer bladder sheet 84". In the illustrated embodiment, the air diverter 170 comprises a thin, flat panel, also designated 170, and two segments or edge margins 170A, 170B of the panel are affixed to the inside surface 174 of the outer bladder sheet 84". Another edge margin 170C of the panel 170 overlies a portion of the bladder opening 78". Thus, the panel 170 is positioned to divert air entering the inflatable chamber 76" from the port 64" through the bladder opening 78" from directly impinging against the impingement surface 120". A portion of the air entering the inflatable chamber 76" through the bladder opening 78" bypasses the edge margin 170C of the panel 170 that overlies the bladder opening and may impinge against the impingement surface 120". The panel 170 channels air entering the inflatable chamber 76 through the bladder opening 78" along an upper surface 170D of the panel 170, between the two segments 170A, 170B affixed to the inside surface 174 of the outer bladder sheet 84". The affixed segments 170A, 170B may be spaced from one another so that the panel 170 is affixed to the outer bladder sheet 84" in a bowed fashion that facilitates flow of air between the panel and the outer bladder sheet.

The panel 170 may be made of a more rigid material (e.g., rigid plastic) relative to the material of the impingement surface 120". Air impinging against the panel 170 creates less noise because air impinging against the more rigid material of the panel creates fewer pressure waves in an audible range than if the air were impinging against the impingement surface 120". Moreover, the bladder opening 78" may be enlarged to overlie a greater portion of the upper surface 170D of the panel 170 so that a larger percentage of the air passing into the inflatable chamber impinges against the panel to further reduce noise during inflation.

The panel 170 is configured to allow air to pass from the inflatable chamber 76" through the bladder opening 78" to deflate the inflatable chamber. In the illustrated embodiment, the panel 170 allows air to pass from the inflatable chamber 76" through the bladder opening 78" because the panel does not overlie substantially all of the bladder opening. If the panel 170 were positioned to overlie substantially all of the bladder opening 78", the panel may act as a check valve that traps air inside the inflatable chamber 76".

In use, the foot cuff 10 is fluidly connected to a compression therapy system (not shown). Compressed air is delivered to the bladder 56 of the foot cuff 10 via the port 64 and bladder opening 78 to apply compressive pressure to a foot of a wearer. Noise attenuating means 30, 30', 30", such as the flaps 140, 150 or the air diverter 170, may be used to reduce the noise generated during inflation of the inflatable chamber.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" at intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A pneumatic compression garment comprising:
a flexible member for placement on a limb of a human body;
a bladder in the flexible member comprising first and second opposing sheets of flexible, air-impermeable material and defining an inflatable chamber, the bladder having an opening through which the inflatable chamber is inflated;
a port affixed to an outside surface of the first sheet, the port having an air inlet adapted for communication with a source of pressurized air and an air outlet in communication with the inflatable chamber via the opening in the bladder for delivery of air from the source of pressurized air into the inflatable chamber for inflating the inflatable chamber and thereby applying a compression force to the limb when the flexible member is in place on the limb; and
an air diverter formed of air-impermeable material, the air diverter affixed to an inside surface of the first sheet, and the air diverter having an edge overlying a portion of the opening in the bladder and configured to divert air entering the inflatable chamber from directly impinging against an inside surface of the second sheet,
wherein the edge of the air diverter overlying a portion of the opening in the bladder divides the opening into a part covered by the air diverter and a part not covered by the air diverter.

2. The pneumatic compression garment of claim 1, wherein the edge of the air diverter overlying at least a portion of the opening in the bladder is between the opening in the bladder and the second sheet.

3. The pneumatic compression garment of claim 1, wherein the air-impermeable material forming the air diverter is more rigid than the material of the first and second sheets.

4. The pneumatic compression garment of claim 1, wherein the air diverter directs air entering the inflatable chamber in a direction nonorthogonal to the first and second sheets.

5. The pneumatic compression garment of claim 1, wherein the air diverter is affixed to the inside surface of the first sheet along a first and a second connecting segment such that air entering the inflatable chamber moves along the air diverter, between the first and second connecting segments.

6. The pneumatic compression garment of claim 1, wherein the edge comprises a perimeter edge of the air diverter, at least a portion of the perimeter edge overlies the opening in the bladder.

7. A pneumatic compression garment comprising:
a flexible member for placement on a limb of a human body;
a bladder in the flexible member comprising first and second opposing sheets of flexible, air-impermeable material and defining an inflatable chamber, the first sheet defining an opening; and
a panel formed of air-impermeable material affixed to an inside surface of the first sheet, the panel having an edge between a portion of the opening in the first sheet and the second bladder sheet such that air entering the inflatable chamber through the opening is diverted from directly impinging against an inside surface of the second sheet,
wherein the edge of the panel overlying a portion of the opening in the first sheet divides the opening into a part covered by the panel and a part not covered by the panel.

8. The pneumatic compression garment of claim 7, wherein the material forming the panel is more rigid than the material of the first and second sheets.

9. The pneumatic compression garment of claim 7, wherein the panel directs air entering the inflatable chamber in a direction nonorthogonal to the first and second sheets.

10. The pneumatic compression garment of claim 7, wherein the panel is affixed to the inside surface of the first sheet along a first and a second connecting segment such that air entering the inflatable chamber moves along the panel, between the first and second connecting segments.

11. The pneumatic compression garment of claim 7, wherein a portion of the air entering the inflatable chamber through the opening bypasses the edge of the panel to directly impinge against the inside surface of the second sheet.

* * * * *